United States Patent
Lee et al.

(10) Patent No.: US 7,210,817 B2
(45) Date of Patent: May 1, 2007

(54) METHOD, SYSTEM AND DEVICE FOR DELIVERING PHOTOTHERAPY TO A PATIENT

(75) Inventors: Kian Shin Lee, Penang (MY); Janet Bee Yin Chua, Penang (MY); Yew Cheong Kuan, Penang (MY); Heng Yow Cheng, Penang (MY); Kee Yean Ng, Penang (MY); Wen Ya Ou, Penang (MY)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 249 days.

(21) Appl. No.: 10/833,905

(22) Filed: Apr. 27, 2004

(65) Prior Publication Data

US 2005/0237739 A1    Oct. 27, 2005

(51) Int. Cl.
*F21V 21/00* (2006.01)
(52) U.S. Cl. ............... 362/249; 362/227; 361/719; 607/2; 607/88; 607/91
(58) Field of Classification Search ............... 362/145, 362/249, 240, 800; 361/719
See application file for complete search history.

(56) References Cited

U.S. PATENT DOCUMENTS

| | | | |
|---|---|---|---|
| 6,290,713 B1 * | 9/2001 | Russell | 607/88 |
| 6,871,981 B2 * | 3/2005 | Alexanderson et al. | 362/294 |
| 6,945,672 B2 * | 9/2005 | Du et al. | 362/241 |
| 6,999,318 B2 * | 2/2006 | Newby | 361/719 |
| 2004/0138726 A1 * | 7/2004 | Savage et al. | 607/88 |
| 2004/0149998 A1 * | 8/2004 | Henson et al. | 257/98 |

FOREIGN PATENT DOCUMENTS

WO    WO 2004087793 A1 * 10/2004

OTHER PUBLICATIONS

Northpoint Technologies, INC. Flexible Circuits [online], [retrieved on Feb. 18, 2006]. Rerieved from the Internet <http://web.archive.org/web/20031030104520/http://www.flexcircuitsinc.com/benefits.htm>.*

* cited by examiner

*Primary Examiner*—Renee Luebke
*Assistant Examiner*—Mary Zettl

(57) ABSTRACT

A system and method for a reverse mounted light array. In one method embodiment, the present invention couples a reverse mounted light-generating source with a substrate. Additionally, the present invention couples an electrical portion of the reverse mounted light generating source with a conductive trace coupled to the reverse side of the substrate, wherein the coupling of the conductive trace with the substrate and the reverse mounted light generating source forms a reverse mounted light array.

34 Claims, 10 Drawing Sheets

400

500

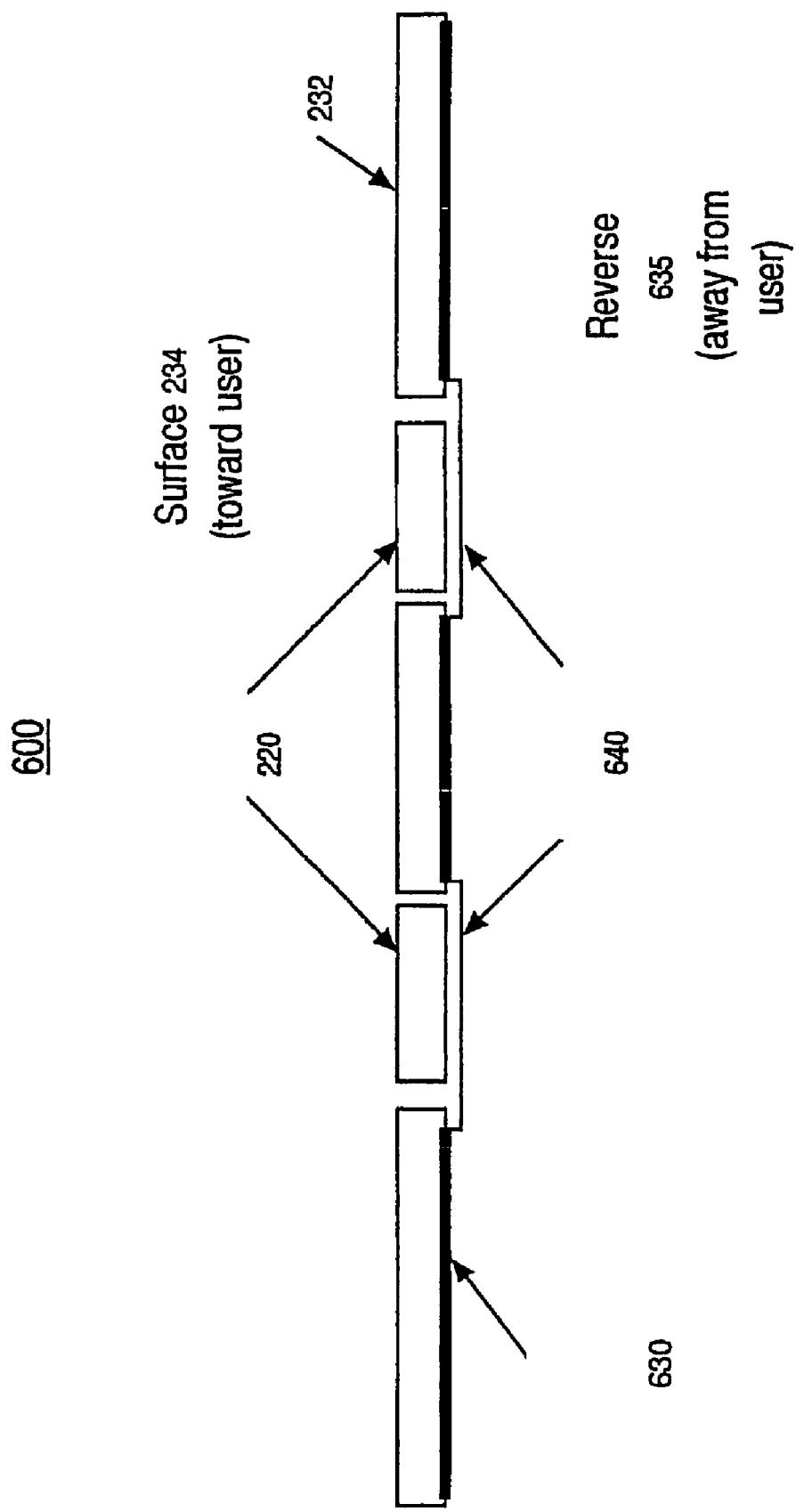

METHOD, SYSTEM AND DEVICE FOR DELIVERING PHOTOTHERAPY TO A PATIENT

FIELD OF INVENTION

Various embodiments of the present invention relate to the field of light emission devices in an array.

BACKGROUND OF THE INVENTION

Light emitting diodes (LEDs) are devices that use a semiconductor diode that emits light when charged with electricity. LEDs provide light in a wide array of electronic devices. For example, LEDs are used as on/off indicators in electronic devices, are used to provide LCD or keypad backlighting in handheld devices, such as personal digital assistants (PDAs) and cellular telephones, and are used for digital display readouts, such as electronic signs. Typically, LEDs are manufactured into an electronic chip (e.g., LED chips) that provide for easy integration into electronic devices.

Moreover, LEDs have found their way into lighting applications, photo-therapeutic applications, and other applications where a compact, low voltage, rugged, and high efficiency light source is advantageous. In many such applications, a number of LEDs are arranged into an array or other pre-determined arrangement having similar or dissimilar LED types.

However, one problem associated with LED illumination array in a phototherapy context is the surface mount of the LED with respect to the substrate. That is, the LED or light source is mounted on top of the flexible substrate and the connections (including wiring, solders, etc.) for the light source are also on top of the flexible substrate.

FIG. 1 illustrates one prior art embodiment that has a substrate 10, an LED 12, and an interface comprising a solid layer 14 of light-diffusing and heat-insulating material. One example of material for the layer 14 is silicone having glass bubbles distributed randomly throughout. Another example of material for the layer 14 is silicone having Titania distributed throughout. Alternatively, or in addition, the layer 14 may be silicone having a matte finish on the skin contact surface 16. The skin contact surface may have a pattern, for example, a printed pattern, effective to scatter and diffuse light.

The backing comprises a solid layer 18 of light-reflective, heat-conductive material including a solid layer of light-diffusive, heat-conductive material. In addition, the backing includes a back cover spaced from a substrate 10 with a secondary spacer having gaps or channels therein directly across the substrate 10 from each of the LEDs 12. The backing also includes a back cover 24 spaced from the substrate 10 with a secondary spacer 25. In this case, the secondary spacer 25 is provided directly underneath each of the LEDs 12, and preferably is made of a highly heat conductive material. Heat thus flows from the LED 12 through the substrate 10 to the secondary spacer 25, which is cooled on either side by the gaps 26.

In the surface mount configuration, a silicone (or other insulating) coating 14 is necessary to stop any fluids or contaminants from contacting the surface of the flexible substrate and having deleterious effects on the circuitry and/or the light source mounted on the substrate surface. Additionally, in the surface mount configuration, the dissipation of heat from the light source can be extremely difficult thereby resulting in a decrease in the light producing capabilities of the light source to ensure that a user is not burned.

SUMMARY OF THE INVENTION

A system and method for reverse mounted light array is disclosed. In one method embodiment, the present invention couples a reverse mounted light-generating source with a substrate. Additionally, the present invention couples an electrical portion of the reverse mounted light generating source with a conductive trace coupled to the reverse side of the substrate, wherein the coupling of the conductive trace with the substrate and the reverse mounted light generating source forms a reverse mounted light array.

BRIEF DESCRIPTION OF THE DRAWINGS

The accompanying drawings, which are incorporated in and form a part of this specification, illustrate embodiments of the invention and, together with the description, serve to explain the principles of the invention:

(Prior Art)

FIG. 6A shows a side view of a reverse mounted light array in accordance with an embodiment of the present invention.

DETAILED DESCRIPTION

The present invention provides a reverse mounted flexible light array having a variety of applications, such as for the treatment of hyperbilirubinemia in neonates, and psoriasis, seasonal affective disorder, sleep disorders, herpes, acne, skin cancer, and other medical conditions. The invention is an advance over current fiber-optic type illumination panels because of the increased intensity of the light-generating sources. Various configurations are described herein, none of which should be construed as particularly preferred in general.

Figure 2:
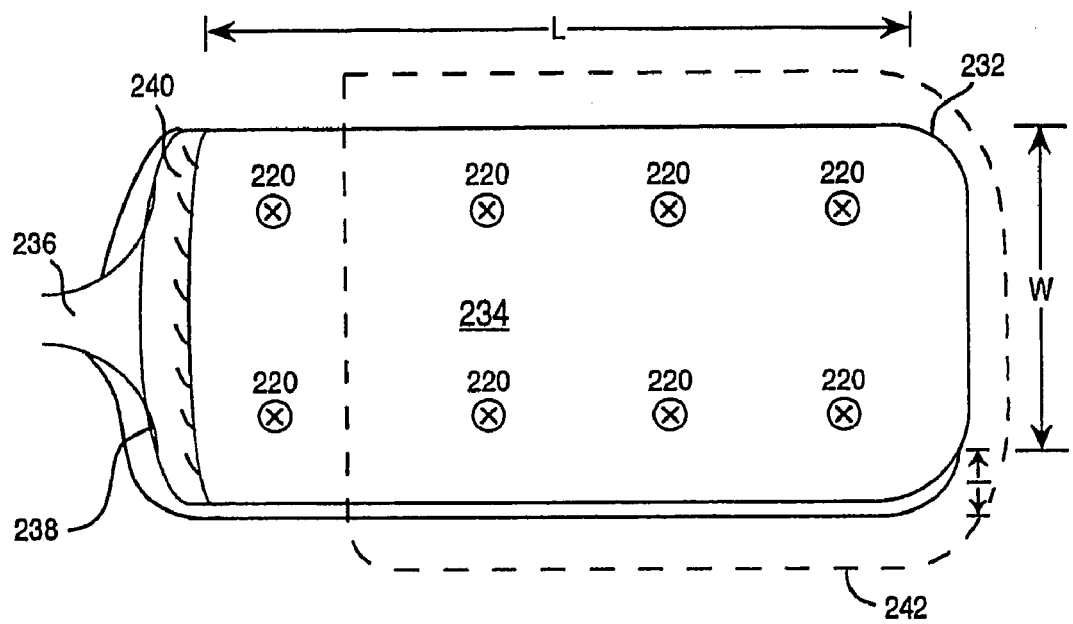
FIG. 2 is a perspective view of a flexible mat-type illumination panel of the present invention.
Figure 3:
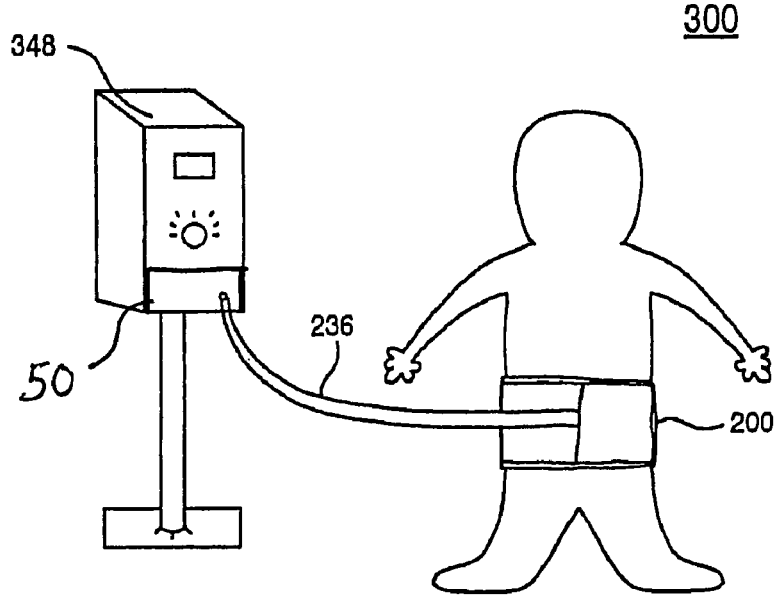
FIG. 3 is a schematic view of a phototherapy system utilizing a flexible mat-type illumination panel of the present invention.
Figure 5:
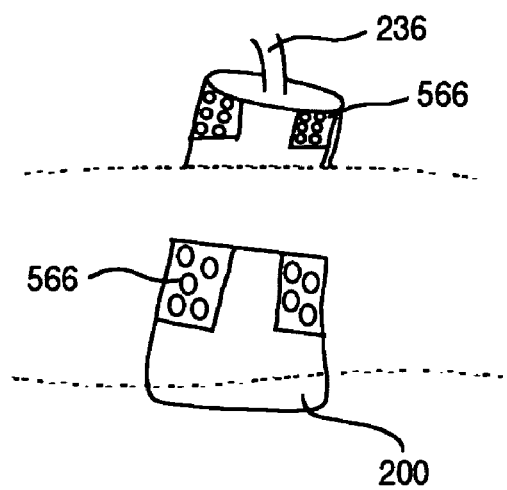
FIG. 5 is a perspective view of a flexible mat-type illumination panel of the present invention wrapped around an adult limb in accordance with an embodiment of the present invention.

With reference now to FIG. 2, in one embodiment, an illumination panel 200 of the present invention having an elongate, planar, flexible body 232 is shown having a front or contact surface 234 and a back surface facing the opposite direction and not seen in FIG. 2. In the embodiment, the illumination panel 200 has a rounded rectangular configuration with a length L, a width W, and a thickness T, with the length L being substantially greater than the width W, both of which are substantially greater than the thickness T. The proportion of these dimensions is preferred to enable the illumination panel 200 to be wrapped around a small infant, or around the limb of an adult, and cover substantial surface area, as seen in FIGS. 3 and 5. Of course, those of skill in the art will understand that other configurations are possible.

As will be describe in more detail below, the illumination panel 200 contains a plurality of electric light-generating sources 220, and thus a power cable 236 attaches to a first narrow end 238 of the body 232. The body 232 is thicker in a region 240 adjacent to the first end 238 to provide strain relief at the interface between the body and cable 236. In one embodiment, the body 232 is molded around the light-generating sources 220 and power cable 236, with the thickened region 240 being formed accordingly. Alternatively, a higher durometer or stiffer material may be used on the end of the illumination panel and/or near the end of the cable to provide the strain relief. As will also be described below, the illumination panel 200 may include means for transferring heat away from the front surface 234, which may involve flow of a cooling medium to interior channels formed in the body 232. In that case, the jacket around the power cable 236 may also provide a conduit for delivery of the cooling medium to and from the illumination panel 200.

As seen in FIG. 2, the illumination panel 200 is desirably at least partly surrounded with a disposable overwrap 242 as a contamination barrier between the illumination panel and the skin of the patient. Such an overwrap 242 may be thin biocompatible polymer, such as polyethylene, polyurethane or cellophane, and is preferably transparent (or at least translucent) so as not to substantially reduce the intensity of light transmitted to the patient. Additionally, the overwrap 242 may have heat insulating and/or light diffusing properties. The overwrap 242 is preferably loosely fitted over the illumination panel in any form, and can be easily secured by tape, elastic or other means, and thus easily removed and disposed of for sanitary purposes. The illumination panel can then be immediately re-used with a second overwrap 242.

Referring now to FIGS. 3, 4, 5 and 5A, several potential configurations of the illumination panel are shown in accordance with embodiments of the present invention. In FIG. 3, an illumination panel 200 similar to that shown in FIG. 2 is wrapped completely around the abdomen of an infant patient. The illumination panel 200 may be secured in this position using straps, hook and pile tape, adhesive tape adhered to a disposable cover, or other such attachment means. A cable 236 supplies electricity and cooling medium from a control housing 348 to illumination panel 200, as mentioned above. FIG. 3 schematically illustrates a control assembly 348 (of conventional design) providing electricity to illumination panel 200 through power conduit 236. Control assembly 348 also controls the operation of an active cooling system 50 including a source of cooling medium and a pump (not shown) cooling system 50 may include cooling coils or other suitable assembly for maintaining the temperature of the cooling medium or coolant at a desired level. A pair of conduits, in one embodiment integrated with cable 236, deliver the cooling medium to the illumination panel 200 and return medium to be cooled to the system 50.

Figure 4:
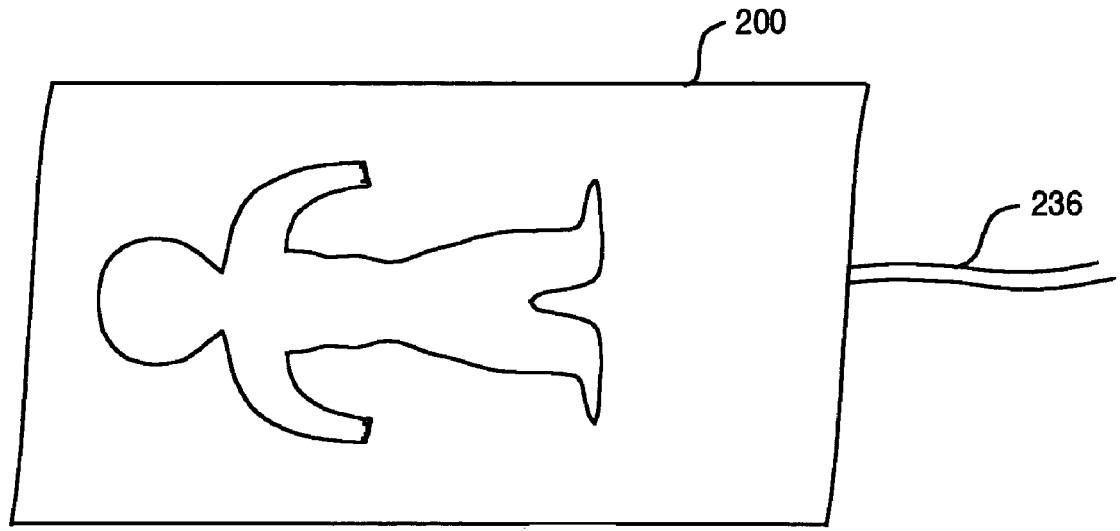
FIG. 4 is a perspective view of alternative mat-type illumination panel of the present invention.

With reference now to FIG. 4, a larger, mat-type illumination panel 200 upon which an infant may be placed is shown. A single cable 236 supplies power (and possibly cooling medium) to the illumination panel 200.

Referring now to FIG. 5, a mat-type illumination panel 200, much like the illumination panel 200 illustrated in FIG. 2, is shown wrapped around the patient's limb and fastened with hook/loop fastener patches 566. Again, a single conduit 236 delivers power and potentially cooling medium to the illumination panel 200.

The illumination panel may be formed into a variety shapes, such as a pad or mat shown, and may be formed into any suitable configuration to treat various medical conditions, as described herein, while also protecting the patient from unwanted, and possibly harmful exposure to light and/or heat. For example, the present illumination panels can be configured to be placed on the face, like a washcloth, for the treatment of seasonal affective disorder, as well as acne and other skin conditions; or can be configured similarly to a sanitary napkin, tampon or condom for the treatment of herpes. Alternatively, the illumination panel can be formed into a belt, a wrap, a cushion or pillow, a collar, a blanket, a strap, a vest, or any other desired shape. Advantageously, the particular shape and ultimate configuration on the patient does not affected the quality and intensity of the light delivered, as with prior fiber optic devices. In short, the forms of the present illumination panels illustrated are not intended, and should not be taken, to be limiting.

With reference now to FIG. 6A, one embodiment of the present invention provides a phototherapy device 600 includes a substrate 232 with a conductive trace 630 coupled therewith and at least one light generating source 220 reversely coupled therewith. The various attributes of the phototherapy device 600 will now be described, followed by a more detailed description of a number of exemplary embodiments. In some cases, the phototherapy device is termed a "reverse mounted light array" herein.

The reverse mounted light array 600 has a substrate 232 having at least one electrically powered light-generating source thereon. In this regard, the substrate 232 may be variety of forms, typically including an insulating body on or in which a plurality of conductive leads or traces are provided. The light-generating source 220 is reversely mounted to the insulating body in electrical communication with the conductive traces 630.

In general, the present invention utilizes any type of substrate 232 circuitry 630 known in the arts including flexible substrate 232 circuitry 630. Typically, the term "flexible substrate" pertains to polymeric sheets, which may be bent or rolled without breaking. In one embodiment, the substrate 232 may be said to be flexible if it can be rolled, without breaking, into a cylindrical tube having a diameter less than 30 cm, and in some cases less than 5 cm. Examples of such flexible substrates 232 are flexible printed circuitry laminates, which are composite of metal conductors and dielectric substrates bonded together by an adhesive system. Other flexible substrates may not use adhesive, such as copper foil, which is electrolytically deposited or rolled-annealed.

In one embodiment, the substrate 232 should be flexible and capable of withstanding the heat generated during the manufacturing process and by the light-generating sources.

Consideration should also be given to the dimensional stability, chemical resistance, electrical properties, flame retardancy, and cost. Substrate can be either thermosetting or thermoplastic polymers, such as polyester and polyamide films. DuPont Kapton® and similar films are often utilized.

Figure 6B:
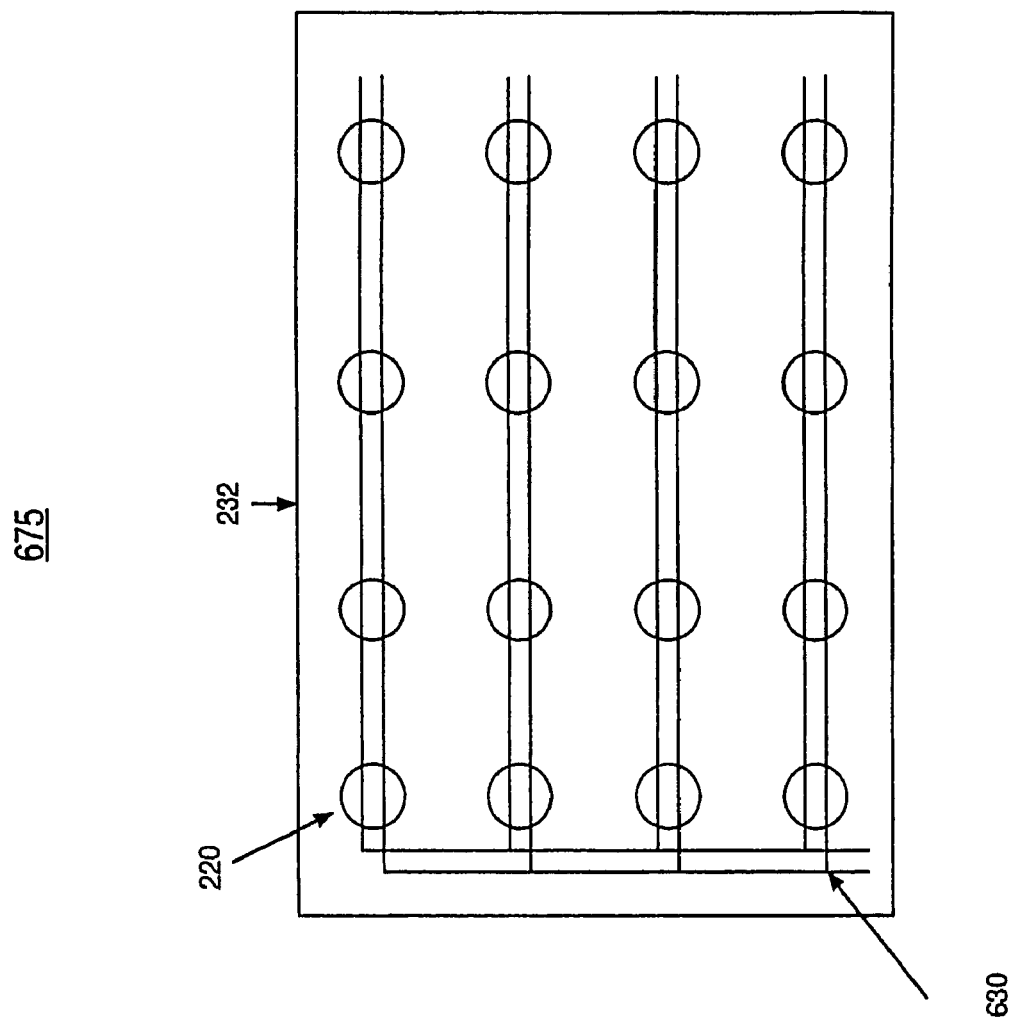
FIG. 6B shows a reverse side view of a reverse mounted light array in accordance with an embodiment of the present invention.

With reference now to FIG. 6B, one embodiment of the reverse side of the reverse mounted array technique is shown. The substrate 232 may be coated, cast, deposited, or otherwise adhered to the conductive tracing 630 or vice versa. In one embodiment, the conductive tracings 630 are directly adjacent to and in contact with the substrate 232. Alternatively, one or more additional layers may be present between the conductive traces 630 and flexible substrate 232, such as when adhesive are used. The conductive tracings 630 may include a variety of materials, including rolled-annealed copper, electro-deposited copper, silver, nickel, gold, aluminum, iron, steel, solder, or any other metal or conductor. The conductive coating may be applied as, processed into, tracings using any means for application or removal, including chemical, mechanical, and optical means, as well as the use of lasers.

In one embodiment, holes are formed in the flexible substrate 232 and each LED 220 is fitted into the hole in the substrate and mounted on the tracks on the reverse 635 of flexible substrate 232. Solder paste is deposited on the exact locations of the anode and cathode tracks using, for example, screening techniques. Thermally conductive glue is also applied to the conductive trace 630 using, for example, dispensing technique. The LED 220 is then coupled with the respective conductive trace 630, with the anode and cathode terminals of the LED 220 corresponding to the solder paste deposited on the anode and cathode tracks of conductive trace 630. The LED 220 is subsequently secured on the conductive trace 630 by any one or more of the plurality of well known light source securing methods. For example, by re-flow soldering of the solder paste and curing the thermally conductive glue, respectively.

In one embodiment, a plurality of pairs of parallel conductive traces are etched into the rolled-annealed copper coating of a flexible substrate, for example, using conventional photo-etching techniques. Polymer thick films including one or more finely divided conductive materials like silver, nickel, or carbon in a polymer binder like polyester, epoxy, acrylic, or vinyl also may be used. Polymer thick film printed wiring is less expensive than copper conductors since it is generally formed in a single step using screen printing, without traditional plating, etching, stripping, and cleaning. Examples of polymer thick films which offer an alternative to other types of circuitry are available from DuPont as the CB® series polymer thick film pastes.

In one embodiment, the light-generating source 220 is a light-emitting diode (LED) chip or die of the reverse mount variety. Reverse mounted LEDs are known in the art. Exemplary off-the-shelf reverse mount LEDs which can be implemented as part of embodiments of the present invention include but are not limited to HSMx-C4A0 LED manufactured and sold by Agilent Technologies, Inc.; SML-811 series light emitting diodes by Rohm; and reverse-mount L-193 series by LEDopto. In another embodiment, the light-generating source 220 may be a light emitting device consisting of a light emitting diode mounted in a cup with electrodes electrically connected and molding material (forming an optical dome or acting as encapsulating material) covering the light emitting diode. Alternatively, other types of reverse mounted LEDs, reverse mounted lasers, and reverse mounted laser diodes may be used. The light-generating source 220 may be multicolored LEDs, or a combination of multiple colored LEDs, a combination of different LEDs, or arrangement of the same type of LEDs, depending on the desired color, distribution or pattern.

For example, for the treatment of neonatal hyperbilirubinemia, the preferred color of LEDs is blue, although green LEDs also may be effective. The treatment of other conditions may require different colored LEDs. For example, herpes may be most effectively treated by red LEDs, seasonal affective disorder may be treated by white or yellow LEDs, and psoriasis may be treated by ultraviolet LEDs.

Referring again to FIG. 6A, due to the reverse mount of the light source 220, a heat sink 640 may be added to the rear of the light source 220 to increase the heat disposition. Specifically, since the light source 220 is reverse mounted to the substrate 232 the problems of dissipation of heat from the light source 220 is greatly reduced in comparison with the surface mount formation. That is, because the light source 220, and therefore the heat sink 640, is mounted at the back of the substrate 232 (e.g., the side furthest from the user) the heat sink 640 is exposed to the environment thereby increasing its heat disposition capabilities. In one embodiment, the heat sink 640 is a copper tap. For example, the heat sink 640 is a circle of copper (or other material) that can be easily attached (e.g., glued, soldered, welded, threaded, stamped, etc.) to the back of light source 220. Although heat sink 640 is stated as a copper tap, heat sink 640 may be made of any thermally dissipating material. Additionally, heat sink 640 may be made of material that is not electrically conductive.

In another embodiment, the heat sink 640 may be attached to the reflector cup 770 of light source 220. In that case, the heat sink 640 contacting the reflector cup 770 (of FIG. 7C) will dissipate the generated heat from the light source 220 via the reflector cup 770 through the heat sink 640 and then to the environment. Due to the increase in heat disposition, a plurality of valuable results may be obtained. For example, since more heat can be dissipated, than by a surface mount light source, the light source 220 of the present invention can be operated at higher power without transferring more heat to the user. Additionally, the need for a silicone coating between the entire substrate 232 and the user is no longer necessary.

Figure 7A:
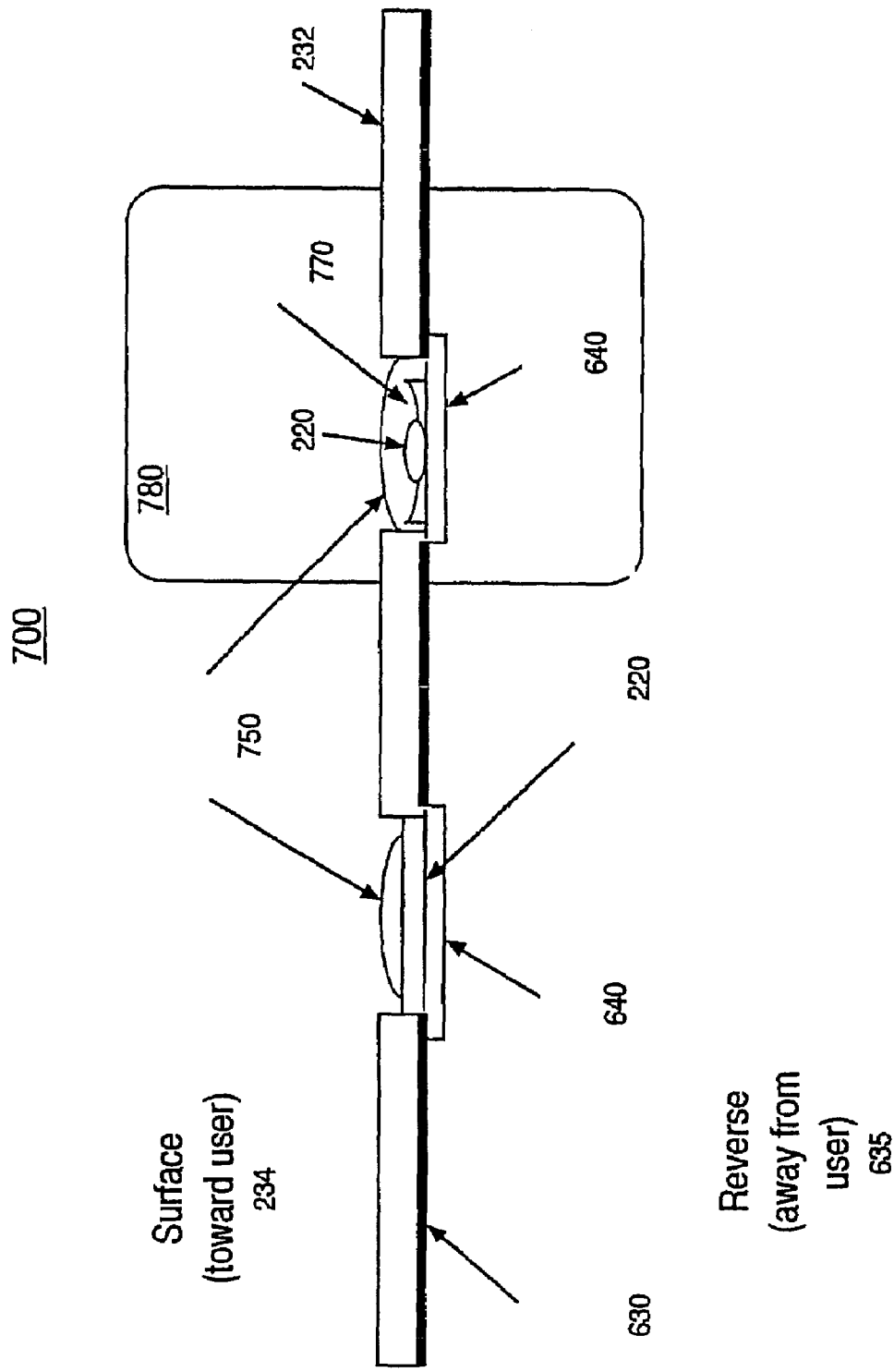
FIG. 7A shows a side view of a reverse mounted light array with optical dome in accordance with one embodiment of the present invention.
Figure 7B:
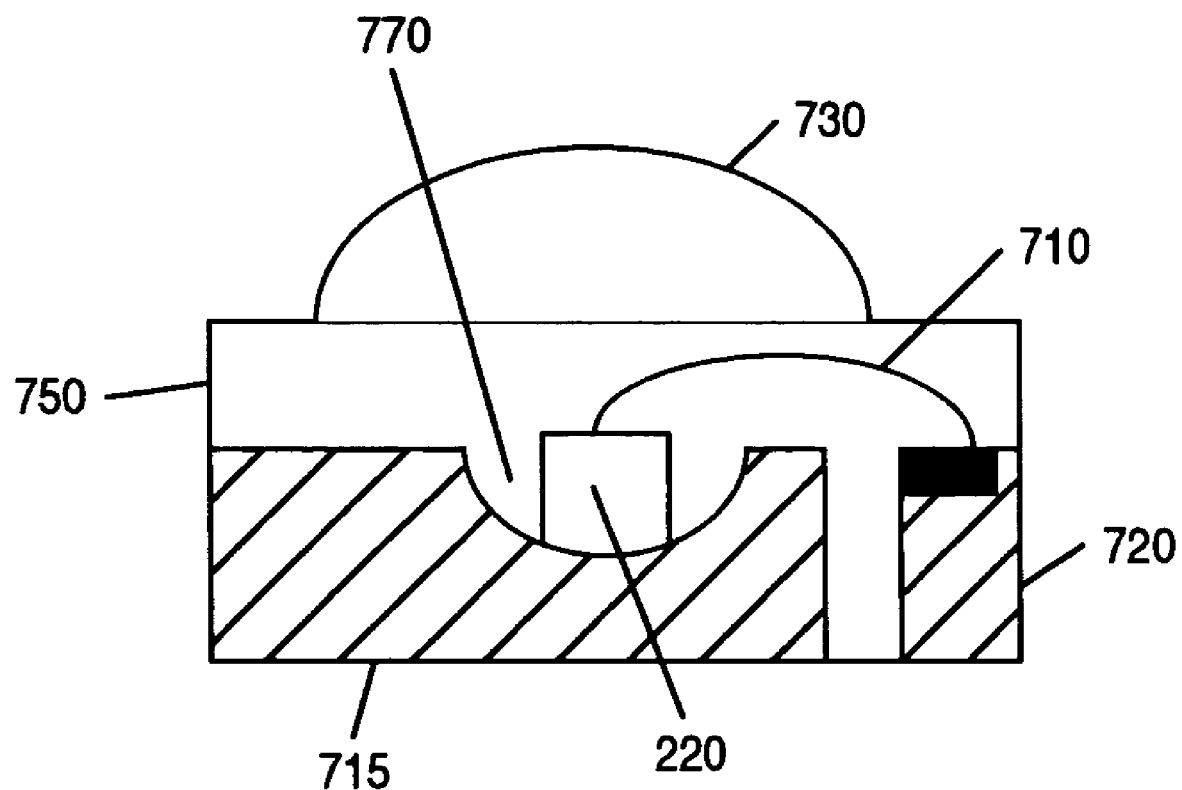
FIG. 7B shows a side view of light emission device including a reflector cup in accordance with an embodiment of the present invention.
Figure 7C:
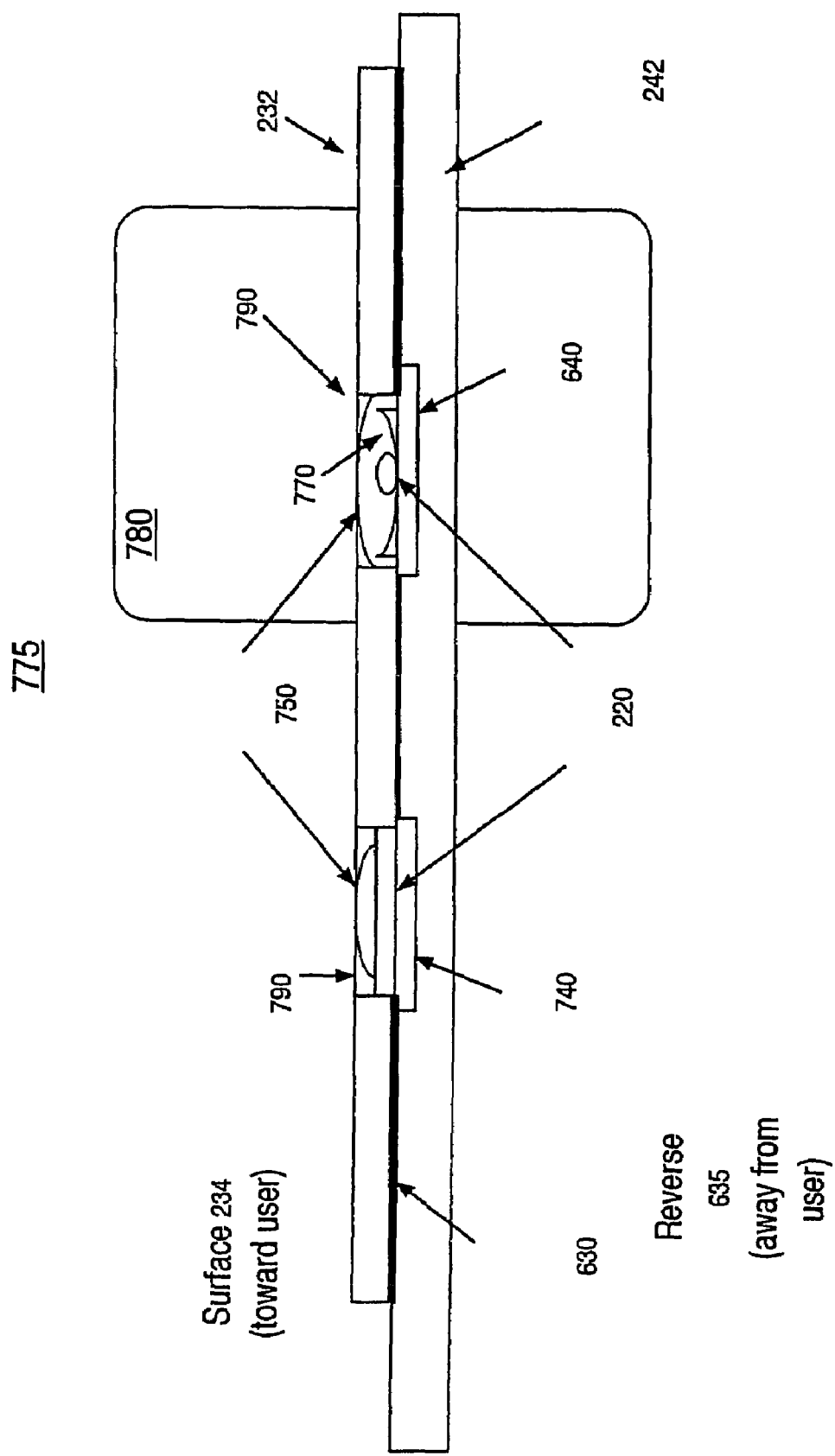
FIG. 7C shows a side view of a reverse mounted light array with optical dome in accordance with another embodiment of the present invention.

In yet another embodiment, as shown in FIGS. 7A through 7C, the reverse mounted LED may be a package LED 780. The package LED 780 may be initially manufactured as one device having a heat sink 640 attached to the reflector cup 770 of light source 220. Thereby making LED package 780 a single manufactured device.

In one embodiment, the reverse mounted light array 600 may include any suitable interconnect technology to provide an electrical circuit among the LEDs, the substrate, the power supply, and any control device. In this regard, flexible or traditional wiring, solder attachment, conductive pieces, and/or pressure connectors may be used.

The reverse mounted light array 600 may also include a controller capable of making the light-generating sources 220 separately addressable so that they may be selectively illuminated in a particular pattern to achieve a particular therapeutic result. In addition, the power level of one or all of the light-generating sources 220 may be controlled to optimize the light intensity required, to mix colors where different LEDs are used, or to shut off light-generating sources 220 in the case of overheating. In the latter instance, thermocouples may be provided in and around the light-generating sources 220, or on the contact surface 234, to monitor the temperature of the reverse mounted light array.

Finally, the reverse mounted light array may contain a timer to assist in metering exposure of the patient according to doctor's instructions.

With reference now to FIG. 7A, in one embodiment an epoxy cast may be formed into a shape, such as a dome, and used for directing light. Optical dome 750 is optically designed based on a software simulation to design the best shape for directing, magnifying, spreading, or otherwise managing the light emitted from the light source 220 and/or reflector cup 770. In one embodiment, optical dome 750 is a round shape dome. It should be appreciated that optical dome 750 may be any shape (e.g., rectangular, triangular, cylindrical), and is not limited to the illustrated embodiment.

In another embodiment, the reverse mounted LED may be a package LED 780. The package LED 780 may be initially manufactured as one device having a heat sink 640 attached to the reflector cup 770 of light source 220 and an optical dome 750 above the reflector cup 770 and light source 220. That is, the LED package is a single manufactured device having a plurality of built in non-removable components.

In one embodiment, optical dome 750 is circular to provide symmetric viewing angles of emitted light in all directions. In another embodiment, optical dome 750 is an oval shaped epoxy dome. By utilizing an oval shape, the light source 220 provides asymmetric viewing angles of emitted light in all directions. For example, using an oval shape dome, the viewing angle on the horizontal axis is greater than the viewing angle on the vertical axis. In general, the LED can be any known LED, for example, an HSMx-C4A0 LED manufactured and sold by Agilent Technologies, Inc.

With reference now to FIG. 7B, a side view of light emission device 760 including a reflector cup 770 is shown in accordance with an embodiment of the present invention. Light emission device 760 comprises light source 220, wire bond 710, and a lead frame comprising first lead frame segment 715 and second lead frame segment 720. Light source 220, wire bond 710 and at least a portion of the lead frame are encased in epoxy cast optical dome 750. It should be appreciated that a lead frame refers to a type of chip package that uses conductive leads that extend outside of a housing. In the present embodiment, a portion of first lead frame segment 715 and a portion of second lead frame segment 720 are not encased within epoxy cast optical dome 750, allowing for the transmission of power signals to light source 220.

In one embodiment, the lead frame is comprised of copper, however, it should be appreciated that any other conductive material, such as another metal, may be implemented. In one embodiment, the lead frame is covered in a plating to improve various properties of the lead frame. For example, plating may be used to improve the bonding strength between light source 220 and first lead frame segment 715 and between wire bond 710 and second lead frame segment 720, may enhance the adhesiveness of epoxy cast optical dome 750 to the lead frame, may prevent oxidization of a metal lead frame, may enhance to solderability of pads of first lead frame segment 715 and second lead frame segment 720, and can improve the surface reflectivity to enhance flux extraction. In one embodiment, the plating is nickel/palladium/gold (NiPdAu). In another embodiment, the plating is silver (Ag). It should be appreciated that any other plating material may be implemented depending on the design requirements of light emission device 760.

A lead frame provides improved thermal dissipation over the use of a PCB substrate, due to the lower thermal resistance. Light emission device 760 can be subjected to higher operating current due to the better heat dissipation properties of the lead frame. Therefore, the luminous intensity of light emission device 760 can be increased. Furthermore, light emission device 760 may have a lower profile due to a lead frame being thinner than a PCB substrate.

Light source 220 is coupled to first lead frame segment 715. In one embodiment, a power signal is received at light source 220 from first lead frame segment 715. In one embodiment, light source 220 is a light emitting diode (LED) die. While embodiments of the invention are described using an LED, it should be appreciated that other types of light sources may be implemented, such as an infrared emitting diode (IRED) or a laser diode. Wire bond 710 is coupled to light source 220 and second lead frame segment 720. Light source 220 receives positive and negative power signals via first lead frame segment 715 and wire bond 710, and emits light in response to such signals. In one embodiment, wire bond 710 is a gold wire. However, it should be appreciated than any conductive material may be implemented at wire bond 710. In one embodiment, first lead frame segment 715 operates as a cathode for transmitting a negative power signal, and second lead frame 720 operates as an anode for transmitting a positive power signal, as indicated at anode mark 730.

Epoxy cast optical dome 750 is formed over light source 220, wire bond 710, a portion of first lead frame segment 715 and an portion of second lead frame segment 720 using an epoxy casting process. The use of a conductive lead frame substrate provides for the use of a conventional casting process in forming epoxy cast optical dome 750. In one embodiment, epoxy cast optical dome 750 is comprised of substantially half epoxy resin and substantially half epoxy hardener. However, it should be appreciated that any combination of epoxy resin and epoxy hardener may be used. Epoxy cast optical dome 750 is translucent, allowing for the passage of light. In one embodiment, epoxy cast optical dome 750 comprises a color tinting for filtering the wavelength of light passing through epoxy cast optical dome 750. In one embodiment, epoxy cast optical dome 750 is operable to diffuse light passing through epoxy cast optical dome 750. Using a casting process to generate epoxy cast optical dome 750 provides a substantial cost savings over transfer molding process due to the high volume per run with high density lead frame design as well as lower initial tooling costs. Furthermore, epoxy cast optical dome 750 provides improved moisture absorption resistivity compared to molding compound which is more sensitive to moisture.

Light emission device 760 comprises reflector cup 770 for receiving light source 220 and for reflecting light emitted from light source 220. In one embodiment, light source 220 resides at least partially within reflector cup 770. Placing light source 220 within reflector cup 770 allows for enhancing and directing the light emitted by light source 220. Furthermore, placing light source 220 within reflector cup 770 assists in providing a low profile for light emission device 760, thereby allowing wider applicability.

Epoxy cast optical dome 750 comprises epoxy shaped portion 730. In the illustrated embodiment, shaped portion 730 is a round shape dome. It should be appreciated that epoxy shaped portion 730 may be any shape and is not limited to the illustrated embodiment. The use of reflector cup 770 in conjunction with epoxy shaped portion 730 allows for directing the light emitted in a desired radiation pattern and viewing angle.

As described above, embodiments of the present invention are configured to implement different types of light sources. For example, embodiments of the present invention may implement a double wire bonded light source (e.g., a double wire bonded LED). A double wire bonded light source is operable to receive positive and negative power signals through two wire bonds, respectively, rather than through one wire bond and through coupling the light source to a lead frame.

Figure 8:
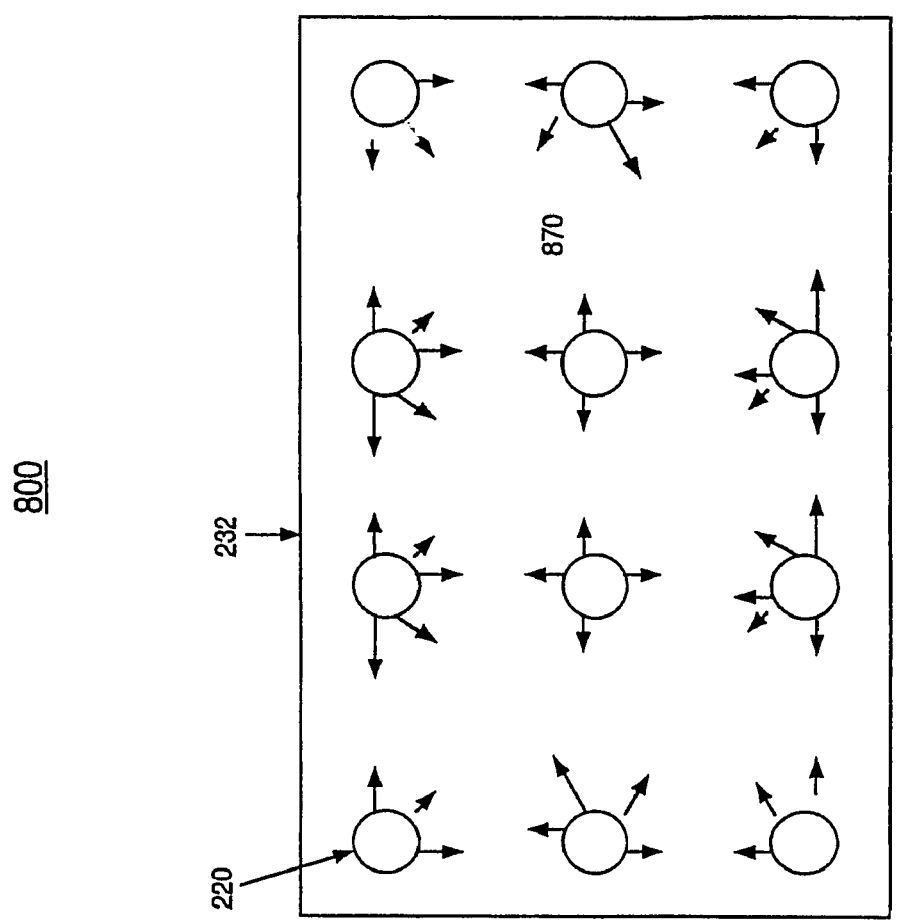
FIG. 8 shows a top view of a reverse mounted light array in accordance with an embodiment of the present invention.

More broadly, at least a portion of the interface causes the light emitted by the plurality of light-generating sources to be diffused or directed as desired such as shown in FIG. 8. Such diffusion or direction is effective to provide a more uniform, constant and intense light pattern on the contact surface relative to a similar apparatus including a plurality of discrete light emitting sources without light diffusion. Therefore, the interface may be made of a single material or blend of materials having different refractive indices, such as silicone and glass bubbles or silicone and titania, or may include other materials, such as metals, to reflect or block light.

Additionally, due to the optical dome 750 directing the light from the light source, an outer covering or an internal layer with deformities or markings formed by mechanical, chemical, or other means to cause light emitted by the light-generating sources 220 to diffuse is not necessary and further reduces the manufacturing and post-manufacturing processing of the reverse mounted light array.

With reference now to FIG. 7C, an optional silicone coating 790 is shown above the optical dome 750. In one embodiment, the silicone coating 790 is used to reduce heat transfer from the light source 220 to the user. Therefore, the silicone coating is just placed above the light source 220. By utilizing a reverse mounted light array, the entire front side of the substrate 232 does not need to be coated in silicone or any other non-conductive material. Since there is no circuitry on the side of the substrate that is facing the user, there is no need to insulate the front side of the substrate 232 from any type of short circuit. Additionally, there is no need to provide a silicone (or other non-conductive bio or non-biometric material) for the protection and/or safety of the user. Therefore, a savings in both manufacture time and cost may be realized.

Moreover, by removing the silicone over-coating, the manufacturer not only realizes a manufacturing cost and time savings, problems inherent with the use of an over-coating are reduced. For example, there is no warping of the substrate 232 due to the heating and cooling of the over-coating material. The substrate 232 may be bent both backward and inward without damaging the substrate 232. There is no worry of discoloration or wear of the over-coating material. Additionally, there are no bubbles or light losses due to light absorption of the over-coating material.

In one embodiment, the reverse side of substrate 232 is covered with an insulation layer 242 such as a cloth layer or other non-conductive material to reduce patient and environment contact. However, this layer differs from the over coating of a surface mount apparatus due to the ability to change or remove the insulation layer 242. In addition, since the light dies not need to pass through insulation layer 242, the material (e.g., neoprene, wool, cotton, etc) used to form insulation layer 242 may be washed, cleaned, supplied separately or the like. Additionally, the insulation layer 242 may be loose or tight and will have little or no effect on the overall flexibility of the reverse mounted light array 775.

With reference now to FIG. 8, a reverse mounted light array 800 is shown according to one embodiment of the present invention. In general, the light array 800 shows the advantages of having the light source 220 optically shaped to provide directed light 870. Specifically, by directing the resultant light from the plurality of light sources 220, the reverse mounted light array 800 will reduce light dissipation thereby increasing efficiency and decreasing power consumption.

Figure 9:
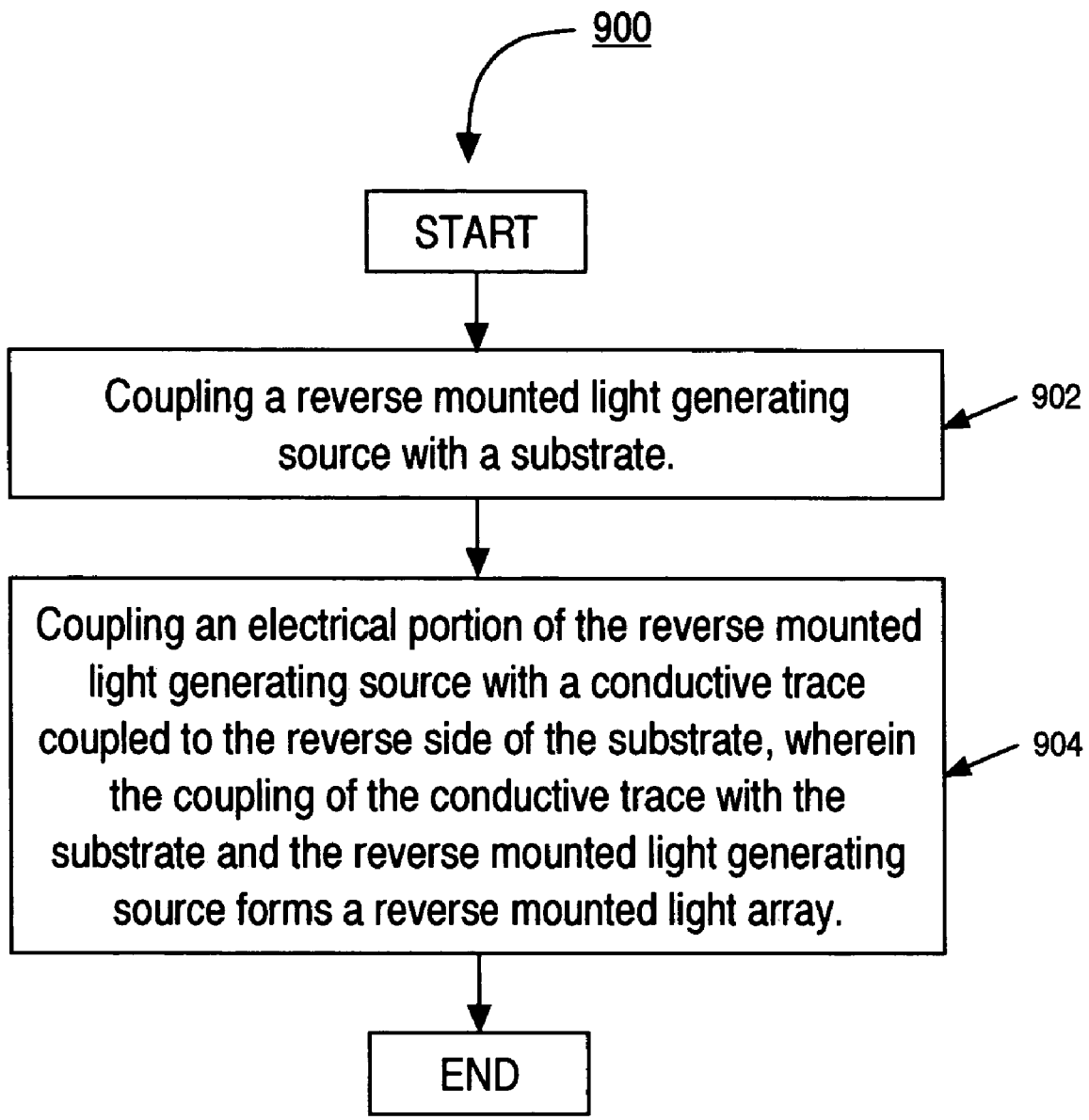
FIG. 9 is a flowchart showing a process for generating a light emission device in accordance with an embodiment of the present invention.

With reference now to FIG. 9, a flow chart showing a process for generating a light emission device in accordance with an embodiment of the present invention.

Figure 1:
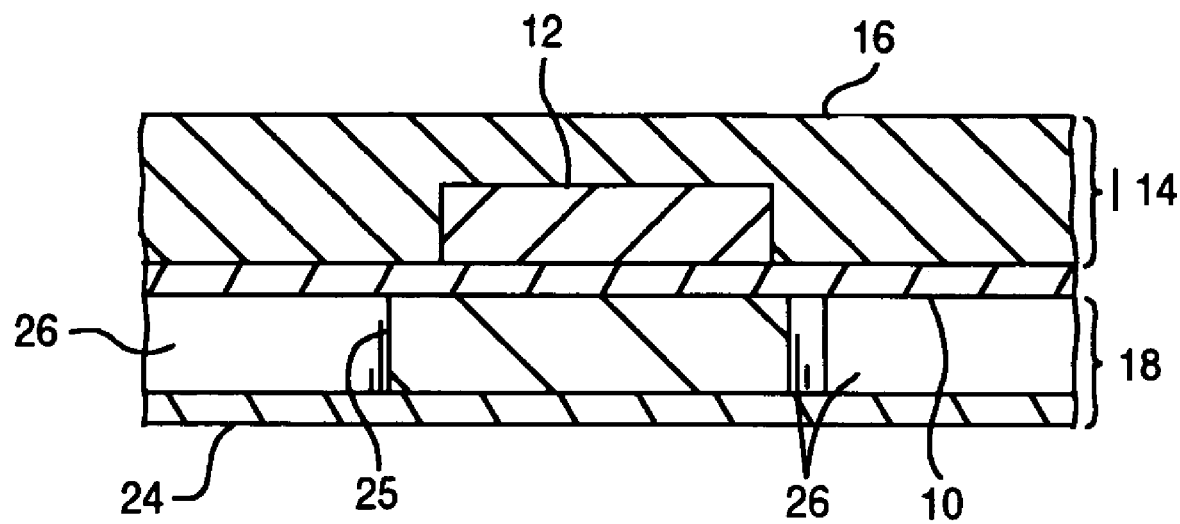
FIG. 1 is a cross-sectional view showing a surface mount LED of the prior art.

Referring now to step 902 of FIG. 9 and to FIG. 1, a reverse mounted light generating source is coupled with a substrate. In one embodiment, the substrate 232 is a flexible substrate such as a flexible circuit, flexible metal frame, or the like, made of polyimide material or the like. In one embodiment, the substrate is an electrically non-conductive but thermally conductive flexible material. In one embodiment, the light source 220 is a low profile, small footprint, high brightness, and high radiometric power light source having a wide viewing angle. In another embodiment, the light source 220 is a light emitting diode (LED), a laser, an organic light emitting diode, or a laser diode, or the like. The light source 220 may be multicolored, a combination of multiple colors, a combination of different light sources 220, or an arrangement of the same type of light sources 220. The pattern and combination of the light source 220 may be modified depending on desired color, distribution, or use of the array 600. In one embodiment, the light generating sources 220 may be attached or embedded into the substrate 232.

Embodiments of the present invention are configured to implement different types of light sources. For example, embodiments of the present invention may implement a double wire bonded light source (e.g., a double wire bonded LED). A double wire bonded light source is operable to receive positive and negative power signals through two wire bonds, respectively, rather than through one wire bond and through coupling the light source to a lead frame.

With reference now to step 904 of FIG. 9 and to FIG. 1, in one embodiment an electrical portion of the reverse mounted light generating source is coupled with a conductive trace coupled to the reverse side of the substrate, wherein the coupling of the conductive trace with the substrate and the reverse mounted light generating source forms a reverse mounted light array. In one embodiment, a plurality of conductive traces 630 are formed on the substrate 232 layer. The conductive trace 630 may be flexible. As shown in FIG. 8, a plurality of discrete light sources 220 may be arranged along the electrical tracks on the flexible substrate layer and may be electrically connected with the electrical tracks of conductive trace 630 such that it is both thin and flexible.

Therefore, embodiments of the invention provide a reverse mounted flexible light array that provides higher operating conditions with better heat dissipation. Furthermore, the reverse mounted flexible light array has improved light management due to the use of directed light technology. The described embodiments also provide a reverse mounted flexible light array that provides higher light output due to the improved heat dissipation, as well as a higher reflective surface, a reflector cup, and a shaped epoxy dome.

Various embodiments of the present invention, a reverse mounted flexible light array, are thus described. While the present invention has been described in particular embodiments, it should be appreciated that the present invention should not be construed as limited by such embodiments, but rather construed according to the below claims.

What is claimed is:

1. A flexible mat for delivering photo-therapy to at least a portion of a body of a patient, comprising:
   (a) a flexible substrate comprising a lower external-facing surface, an upper patient-facing surface, and a plurality of apertures disposed through the substrate and extending between the external-facing surface and the patient-facing surface;
   (b) a plurality of reverse-mount LED packages configured for mounting and positioning on the external-facing surface of the substrate over corresponding apertures such that the LEDs thereof emit light upwardly through or from such apertures substantially in a first direction towards the patient-facing surface of the substrate, each such package further being configured to dissipate heat primarily downwardly in a second direction away from the external-facing surface of the substrate, wherein light-projecting portions of the reverse-mount LED packages extend upwardly through the apertures substantially no further than a plane defined by the patient-facing surface of the substrate, and
   (c) a plurality of at least partially flexible electrically conductive traces operatively connected to the reverse-mount LED packages to provide electrical power, and optionally control signals, thereto.

2. The flexible phototherapy mat of claim 1, further comprising heat sinks thermally connected to the reverse-mounted LED packages.

3. The flexible phototherapy mat of claim 2, wherein the heat sinks are operatively attached to the externally-facing surfaces of the packages.

4. The flexible phototherapy mat of claim 1, wherein the mat forms an elongate, planar body.

5. The flexible phototherapy mat of claim 1, wherein the mat is configured to operate as at least one of a washcloth, a face cloth, a sanitary napkin, a tampon, a condom, a belt, a wrap, a cushion, a pillow, a collar, a blanket, a strap and a vest.

6. The flexible phototherapy mat of claim 1, further comprising a backing layer disposed below the external-facing surface of the substrate.

7. The flexible phototherapy mat of claim 6, wherein the backing layer comprises at least one of a light-reflecting material, a thermally conductive material, a thermally insulative material, an electrically insulative material, a thermosetting material, a thermoplastic material, polyimide, polyester, and a polymeric material.

8. The flexible phototherapy mat of claim 1, further comprising a front layer disposed above the patient-facing surface of substrate.

9. The flexible phototherapy mat of claim 8, wherein the front layer comprises at least one of a light-diffusing material, a light-refracting material, a light-reflecting material, a thermally conductive material, a thermally insulative material, an electrically insulative material, a thermosetting material, a thermoplastic material, polyimide, polyester, and a polymeric material.

10. The flexible phototherapy mat of claim 1, wherein the flexible conductive traces are attached to or mounted on the external-facing surface of the substrate.

11. The flexible phototherapy mat of claim 10, wherein the flexible conductive traces are attached to the external-facing surface of the substrate by an adhesive or an intervening layer.

12. The flexible phototherapy mat of claim 1, wherein the partially flexible electrically conductive traces comprise at least one of a flexible circuitry laminate, a copper foil, a rolled-annealed copper coating disposed on the substrate, an electrically conductive polymer, an electrically conductive thick film, and an electrically conductive paste.

13. The flexible phototherapy mat of claim 1, wherein the reverse-mount LED packages are connected to the electrically conductive traces by at least one of flexible wiring, traditional wiring, solder attachment, conductive pieces, pressure connectors, and flexible metal frames.

14. The flexible phototherapy mat of claim 1, further comprising at least one optical device selected from the group consisting of a magnifier, a spreader, a diffuser, a refractor, a lens, a cup, a dome, a reflector, an epoxy cast, and an encapsulant, where the optical device is operatively associated with LEDs of the reverse-mount LED packages so as to direct or spread light emitted therefrom substantially in the first direction, the optical device further being mounted at or below the plane defined by the patient-facing surface of the substrate.

15. The flexible phototherapy mat of claim 1, wherein the plurality of reverse-mount LED packages comprise at least one of blue LEDs, green LEDs, red LEDs, yellow LEDs, white LEDs, and ultraviolet LEDs.

16. The flexible phototherapy mat of claim 1, further comprising cooling channels disposed therein.

17. The flexible phototherapy mat of claim 1, further comprising a controller for at least one of selectively illuminating, controlling the light intensity, mixing colors, changing the illumination pattern, timing out, and shutting off the LEDs of the reverse-mount LED packages.

18. The flexible phototherapy mat of claim 1, further comprising an active cooling system comprising a source of cooling medium and a pump.

19. The flexible phototherapy mat of claim 1, further comprising at least one of an overwrap, a disposable overwrap, a translucent overwrap, a transparent overwrap, a heat-insulating overwrap, and a light-diffusing overwrap.

20. The flexible phototherapy mat of claim 1, further comprising at last one of a strap, VELCROTM™, and adhesive tape for securing the mat to the portion of the patient's body.

21. A method of making a flexible mat for delivering photo-therapy to at least a portion of a body of a patient, the mat comprising a flexible substrate comprising a lower external-facing surface, an upper patient-facing surface, and a plurality of apertures disposed through the substrate and extending between the external-facing surface and the patient-facing surface, a plurality of reverse-mount LED packages configured for mounting and positioning on the external-facing surface of the substrate over corresponding apertures such that the LEDs thereof emit light upwardly through or from such apertures substantially in a first direction towards the patient-facing surface of the substrate, and wherein light-projecting portions of the reverse-mount LED packages extend upwardly through the apertures substantially no further than a plane defined by the patient-facing surface of the substrate, each such package further being configured to dissipate heat primarily downwardly in a second direction away from the external-facing surface of the substrate, and a plurality of at least partially flexible electrically conductive traces operatively connected to the reverse-mount LED packages to provide electrical power, and optionally control signals, thereto, the method comprising:
   (a) providing the substrate;
   (b) providing the reverse-mount LED packages;

(c) providing the electrically conductive traces, and (d) operatively connecting the substrate, reverse-mount LED packages and the electrically conductive traces to one another.

22. The method of claim 21, further comprising attaching heat sinks thermally to the reverse-mounted LED packages.

23. The method of claim 21, wherein the mat is configured to operate as at least one of a washcloth, a face cloth, a sanitary napkin, a tampon, a condom, a belt, a wrap, a cushion, a pillow, a collar, a blanket, a strap and a vest.

24. The method of claim 21, further comprising providing a backing layer and disposing same below the external-facing surface of the substrate.

25. The method of claim 21, wherein the backing layer comprises at least one of a light-reflecting material, a thermally conductive material, a thermally insulative material, an electrically insulative material, a thermosetting material, a thermoplastic material, polyimide, polyester, and a polymeric material.

26. The method of claim 21, further comprising providing a front layer and disposing same above the patient-facing surface of substrate.

27. The method of claim 21, wherein the front layer comprises at least one of a light-diffusing material, a light-refracting material, a light-reflecting material, a thermally conductive material, a thermally insulative material, an electrically insulative material, a thermosetting material, a thermoplastic material, polyimide, polyester, and a polymeric material.

28. The method of claim 21, further comprising attaching or mounting the flexible conductive traces to or on the external-facing surface of the substrate.

29. The method of claim 28, wherein the flexible conductive traces are attached to the external-facing surface of the substrate by an adhesive or an intervening layer.

30. The method of claim 21, wherein the partially flexible electrically conductive traces comprise at least one of a flexible circuitry laminate, a copper foil, a rolled-annealed copper coating disposed on the substrate, an electrically conductive polymer, an electrically conductive thick film, and an electrically conductive paste.

31. The flexible phototherapy mat of claim 21, further comprising at least one optical device selected from the group consisting of a magnifier, a spreader, a diffuser, a refractor, a lens, a cup, a dome, a reflector, an epoxy cast, and an encapsulant, where the optical device is operatively associated with LEDs of the reverse-mount LED packages so as to direct or spread light emitted therefrom substantially in the first direction, the optical device further being mounted at or below the plane defined by the patient-facing surface of the substrate.

32. The method of claim 21, further comprising providing cooling channels in the mat.

33. The method of claim 21, further comprising providing a controller for at least one of selectively illuminating, controlling the light intensity, mixing colors, changing the illumination pattern, timing out, and shutting off the LEDs of the reverse-mount LED packages and operatively connecting same to the mat.

34. A method of providing phototherapy to at least a portion of a body of a patient using a phototherapy mat, the mat comprising a flexible substrate comprising a lower external-facing surface, an upper patient-facing surface, and a plurality of apertures disposed through the substrate and extending between the external-facing surface and the patient-facing surface, a plurality of reverse-mount LED packages configured for mounting and positioning on the external-facing surface of the substrate over corresponding apertures such that the LEDs thereof emit light upwardly through or from such apertures substantially in a first direction towards the patient-facing surface of the substrate, wherein light-projecting portions of the reverse-mount LED packages extend upwardly through the apertures substantially no further than a plane defined by the patient-facing surface of the substrate, each such package further being configured to dissipate heat primarily downwardly in a second direction away from the external-facing surface of the substrate, and a plurality of at least partially flexible electrically conductive traces operatively connected to the reverse-mount LED packages to provide electrical power, and optionally control signals, thereto, the method comprising:

(a) placing the mat in operative relation to the at least portion of the body of the patient, and (b) electrically energizing the LEDs of the reverse-mount LED packages.

* * * * *